(12) United States Patent
Marchese et al.

(10) Patent No.: US 11,452,883 B1
(45) Date of Patent: Sep. 27, 2022

(54) HANDS-FREE LED DEVICE FOR THE TREATMENT OF WRINKLES, ACNE, OR HAIR LOSS

(71) Applicants: Stephen James Marchese, Las Vegas, NV (US); Chasen James Marchese, Irvine, CA (US)

(72) Inventors: Stephen James Marchese, Las Vegas, NV (US); Chasen James Marchese, Irvine, CA (US)

( * ) Notice: Subject to any disclaimer, the term of this patent is extended or adjusted under 35 U.S.C. 154(b) by 0 days.

(21) Appl. No.: 17/681,704

(22) Filed: Feb. 25, 2022

(51) Int. Cl.
*A61N 5/06* (2006.01)

(52) U.S. Cl.
CPC ......... *A61N 5/0616* (2013.01); *A61N 5/0617* (2013.01); *A61N 2005/0626* (2013.01); *A61N 2005/0633* (2013.01); *A61N 2005/0642* (2013.01); *A61N 2005/0652* (2013.01); *A61N 2005/0663* (2013.01)

(58) Field of Classification Search
CPC ............... A61N 5/0616; A61N 5/0617; A61N 2005/0626; A61N 2005/0633; A61N 2005/0642; A61N 2005/0652; A61N 2005/0663
See application file for complete search history.

(56) References Cited

U.S. PATENT DOCUMENTS

| | | | |
|---|---|---|---|
| 9,913,994 B2 | 3/2018 | Marchese et al. | |
| 10,363,434 B2 | 7/2019 | Marchese et al. | |
| 2004/0138726 A1* | 7/2004 | Savage, Jr. | A61N 5/0621 607/88 |
| 2014/0316492 A1* | 10/2014 | Min | A61N 5/0613 607/91 |
| 2016/0175609 A1* | 6/2016 | Dye | A61N 5/0616 607/90 |
| 2020/0306555 A1* | 10/2020 | Ebbesson | A61N 5/0614 |

* cited by examiner

*Primary Examiner* — Brian T Gedeon
*Assistant Examiner* — Joshua Andrew Schum-Houck

(57) ABSTRACT

A hands-free LED device for the treatment of wrinkles and acne, or hair loss, includes a curved housing. Rigid areas contain the LED bulbs. The LED bulbs are interspaced therebetween the flexible areas; such that between each of the rigid LED bulb areas is a flexible area. The rigid LED bulb areas are between the flexible areas. A leg is provided on opposite sides of the housing, The legs being wider at the top of each leg and narrower at the bottom. The number of LED bulbs at each wavelength for treatment of wrinkles are: 126 LED bulbs of 605 nm; 210 LED bulbs of 630 nm, 126 LED bulbs of 660 nm, and 26 LED bulbs of 850 nm. The number of LED bulbs at each wavelength for treatment of acne are 280 LED bulbs at 415 nm and 210 LED bulbs of 630 nm. Hair loss uses 500-700 LED bulbs at 630 nm.

20 Claims, 11 Drawing Sheets

HANDS-FREE LED DEVICE FOR THE TREATMENT OF WRINKLES, ACNE, OR HAIR LOSS

CROSS-REFERENCE TO RELATED APPLICATIONS

None

FEDERALLY SPONSORED RESEARCH

None

BACKGROUND

Field of the Invention

The invention relates to the general field of hands-free medical treatment of acne, wrinkles, or hair loss. Specifically, the present invention relates to the field of using light emitting diode (LED) LED bulbs in a hands-free device for treating acne, wrinkles and hair loss. Moreover, the present invention relates to the use of light emitting diodes of varying wavelengths and at varying distances from the face of a patient to treat acne and wrinkles for the entire face of a patient being treated.

Description of the Related Art

By way of background, it has been known to Applicant to treat acne or wrinkles using light emitting diodes, through the use of an LED Therapy Bed or a hand-held device.

There are patents relating to the above-described technology; see U.S. Pat. Nos. 10,363,434 and 9,913,994, both invented by and owned by Applicant. In the general field of this patent application, none of the above-listed devices, alone or in any combination, teach or suggest the claimed invention, as set forth, infra, which is directed to a hands-free LED treatment device which treats acne, wrinkles, or hair loss.

SUMMARY OF THE INVENTION

The invention includes an LED array which provides a rigid-flex LED printed circuit board. Typically, manufacturers of printed circuit boards opt for a "flexible" LED printed circuit board for devices which have a curvature. The problem with this construction is that LED bulbs cannot be used on a flexible circuit board. The reason is that when the printed circuit board is flexed, the LEDs crash into one another and break, which forces the use of surface mounted LEDs instead of LED bulbs. This causes two problems. The first problem is that surface mount LEDs are not able to be custom ordered with as wide a variety of custom specifications as an LED bulb. The second problem is that the solder joints holding the surface mount LEDs to the printed circuit board typically crack with usage because of the constant flexing of the printed circuit board. The rigid-flex board, of the present invention overcomes these two problems in the prior art, by allowing usage of LED bulbs in the rigid sections of the printed circuit board, while at the same time giving the LED bulbs some space between the rigid LED sections of the board by separating them with flexible sections that does not have an LEDs therein. These flexible sections also allow for a shape to be formed that results in the LEDs being encased in a plastic curved housing with the curved frame containing both the rigid and flexible areas that permit the use of LED bulbs without the LEDs being damaged over time or amount of use.

In addition to the curved rigid-flex structure holding the LEDs inside the housing, the Hands-Free LED Device for the treatment of wrinkles, acne, or hair loss, for the entire face; supporting the bottom of the housing, on each side of the LED bulb support structure housing which encases the rigid-flex LED bulbs, is a downwardly extending leg which provides for a lower portion that abuts a shoulder of the patient being treated; in order to adjust the spacing of the LED bulbs with respect to the face and head of the patient. The legs are adjustable by a hinge mechanism which allows the legs to widen or narrow the distance of the LED bulbs closer to or further from the head and face of the patient being treated, to maximize the best possible treatment of the patient. Thus, the flexible areas each abut an edge of a rigid area, as discussed, infra. Each of the rigid areas contain a large number of LED bulbs, while the abutting flexible areas prevent the LED bulbs from breaking, in addition, the flexible areas allow the housing to be maintained in a fixed position. There are several areas with the LED bulbs having interspaced therebetween flexible areas; such that between each of the rigid LED bulb areas is a flexible area that keeps each of the rigid areas separate from the flexible areas. The housing is configured to have the LED bulbs both above and surrounding the face and head of a patient being treated. The legs are provided which extend below the bottom of the housing, with the legs being wider at the top of each lea and narrower at the bottom of each leg. LED bulbs are located in the rigid areas of the housing.

For wavelengths for treatment of wrinkles are 605 nm, 630 nm, 660 nm, and 850 mn; and the number of LED bulbs at each wavelength for treatment of wrinkles are: 126 LED bulbs of 605 nm; 210 LED bulbs of 630 nm, 126 LED bulbs of 660 nm, and 126 LED bulbs of 850 nm. More or less LED bulbs may be used for wrinkles instead of the specific numbers of LED bulbs referred to.

For treatment of acne, two different wavelengths are used. The two wavelengths are 414 nm and 630 nm. The number of LED bulbs at each wavelength for treatment of acne are 280 LED bulbs at 415 nm and 210 LED bulbs of 630 nm. More or less LED bulbs may be used for acne instead of the specific numbers of LED bulbs referred to. With respect to treating hair loss, all of the LED bulbs are at the same wavelength of 630 nm. The number of LED bulbs is 500-700 LED bulbs. In one embodiment, the device has the LED bulbs for treatment of wrinkles and acne, and either can be chosen on the control panel. To treat hair loss, the LED bulbs for wrinkles or acne are replaced by LED bulbs for hair loss, at the numbers and wavelengths discussed above. As an alternative, the LED bulbs for acne or wrinkles are placed in one device and the LED bulbs for hair loss are placed in a separate device. In addition, the size of the legs are configured to nave the bottom or the legs abut the patent's shoulders. The size of the housing is configured to cover the entire face and the head of the patient being treated; the legs are connected to the housing by hinges and the hinges are adjustable to raise or lower the height of the housing closer to or further from the face and head of the patient being treated, depending on the treatment being performed.

DETAILED DESCRIPTION EXEMPLARY EMBODIMENTS OF THE INVENTION

Figure 1:
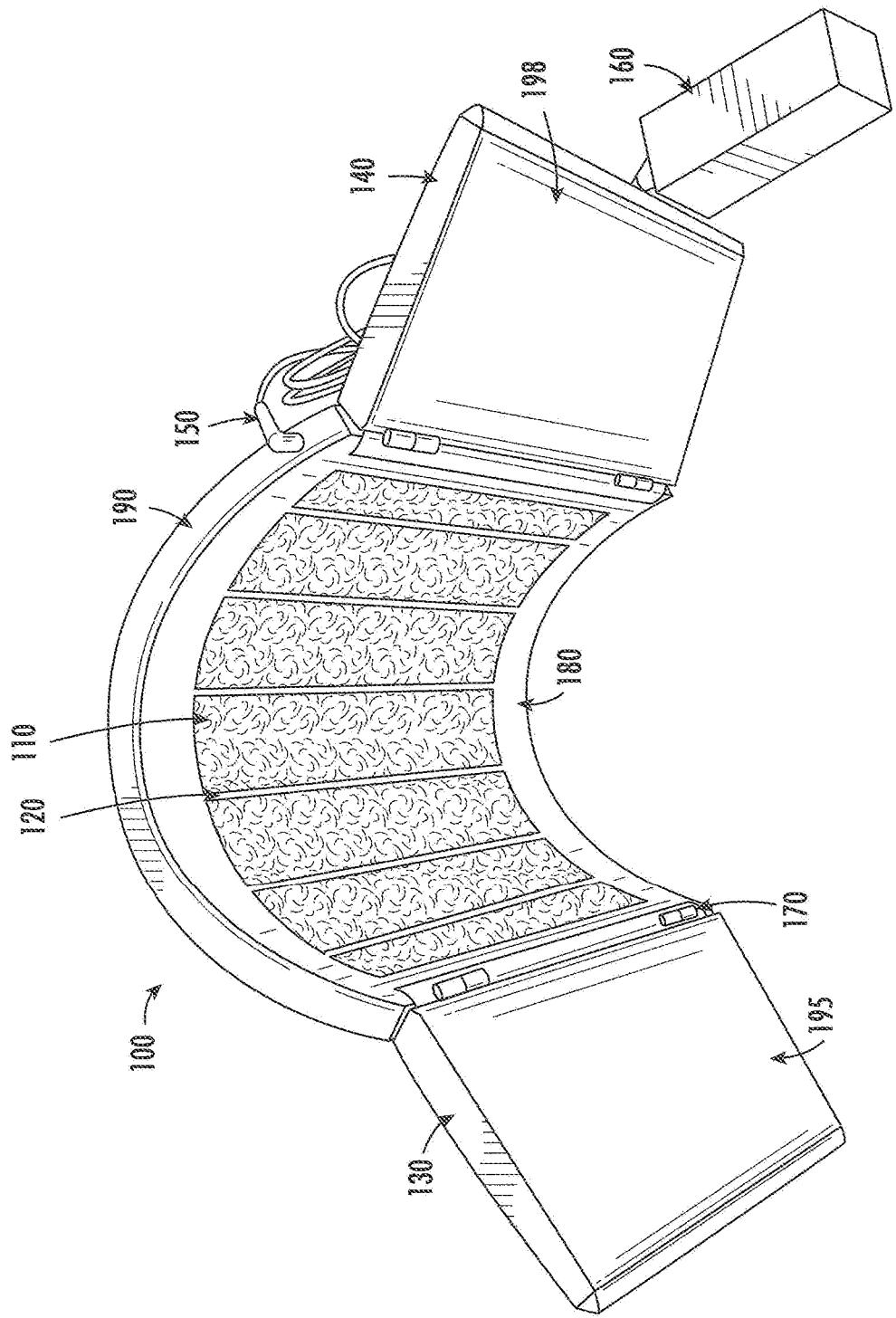
FIG. 1 is directed to a front perspective view of the curved LED bulb housing and the legs that extend therefrom, in an upstanding position.

FIG. 1 illustrates a perspective view of the invention, labeled 100, which has a curved frame 190 at the top of the device and a curved frame 180 located at the bottom of the device. Inside the curved housing are areas of LED bulbs 110 mounted on a rigid backing structure, to prevent breakage. Several separate vertical areas of the LED bulbs are illustrated. Between each of the areas of LED bulbs are narrow vertical areas 120 that are flexible. The narrow vertical areas 120 connect to both 190 at the top of the housing and to 180 at the bottom front of the housing. The flexibility of these areas 120 and the curved structure of both the top and bottom areas 180 and 190 result in the LED bulbs being mounted to tire rigid structure and the narrow vertical areas, located between the rigid areas, being flexible. This gives the LED bulbs some space between the rigid LED sections of the printed circuit board by separating the rigid sections with flexible sections that do not contain any LEDs. This provides the rigid-flex areas with the rigid LED bulb areas 110 and the flexible areas 120 therebetween. The flexible sections also allow for a shape to be formed that the device is eventually fixed in it's encasement in the curved top, which may be plastic or made from other materials, which would be understood by an artisan.

Figure 3:
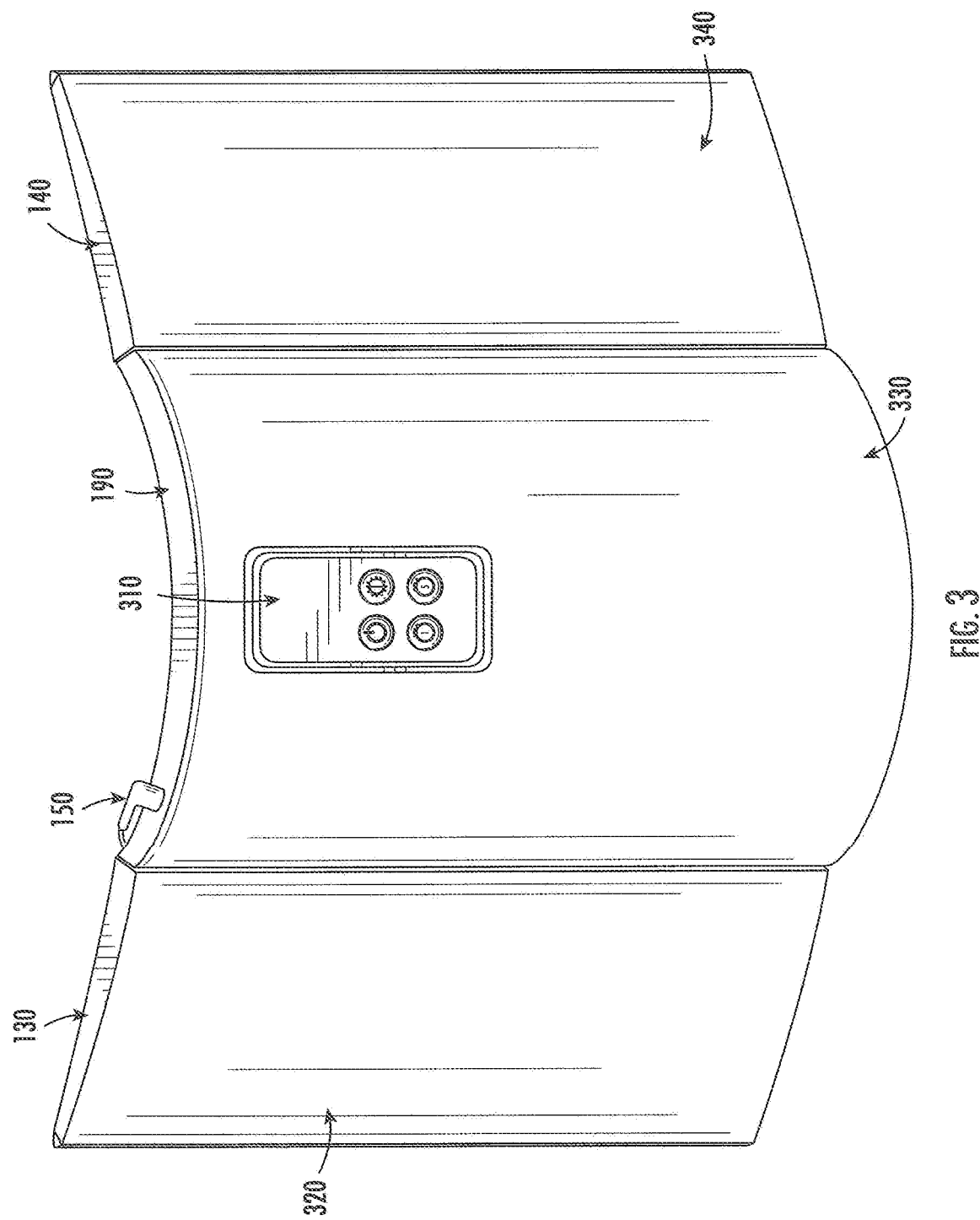
FIG. 3 is directed to a rear view of the invention; showing the control panel.

Additionally illustrated in FIG. 1 are adjustable hinges 170 that connect the movable legs 195 and 198 to the housing 330 (see FIG. 3). Moreover, the top of leg 195 is labeled 130 and the top of the leg 198 is labeled 140. Further illustrated is connector plug 150 for power supply 160. The power supply is shown with battery 160 but can alternately be an electric wall plug, or similar structure, which would be readily understood by one of ordinary skill in the art. Although seven rigid areas filled with LED bulbs are illustrated, the number of rigid LED bulb areas can be more or less, as would be readily understood to one of ordinary skill in the art.

Figure 2:
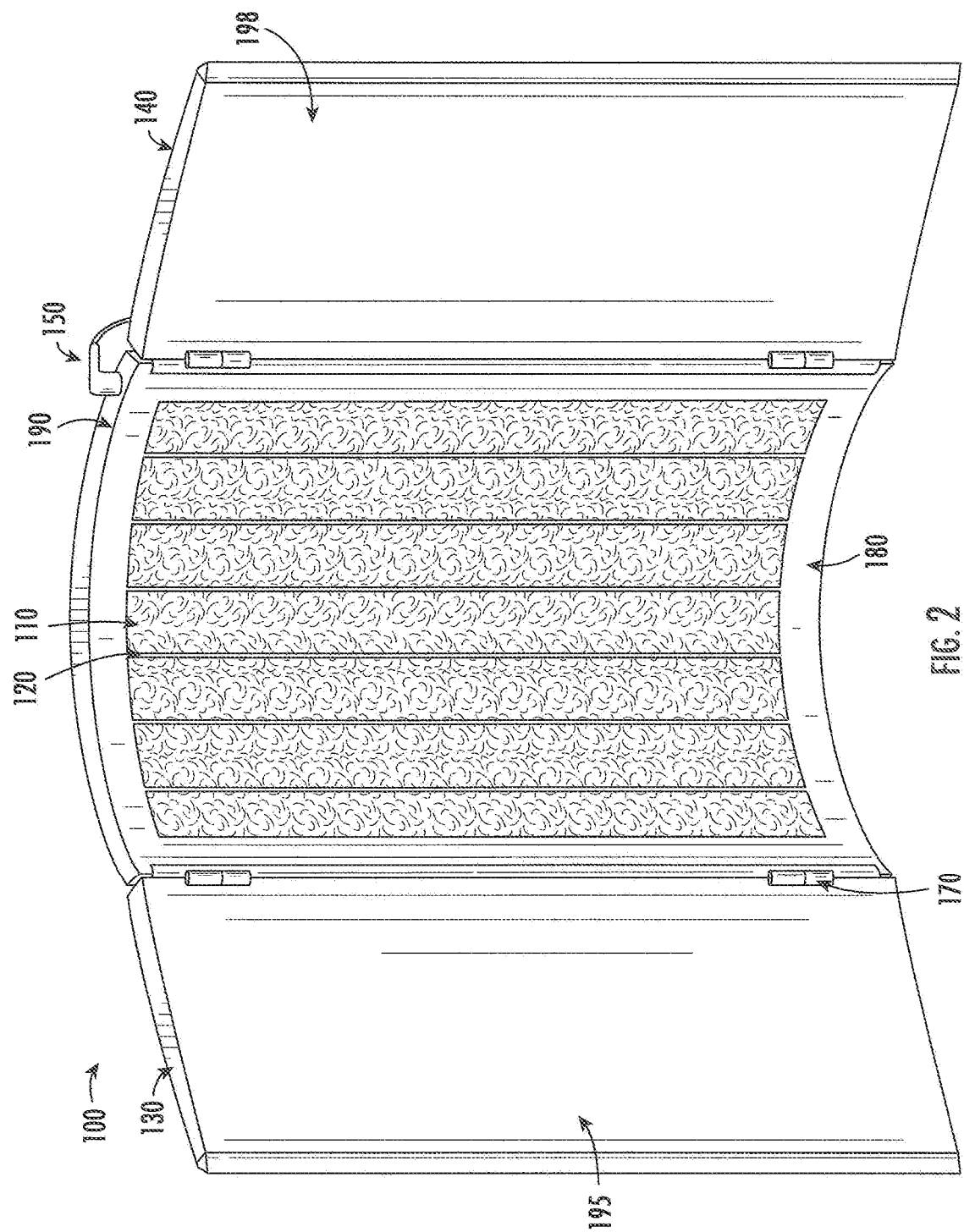
FIG. 2 is directed to a front view of the invention, standing vertically.

FIG. 2 is directed to a front view of the invention, standing vertically so that the LED bulb rigid areas face forward instead of facing downwardly towards the patient. In FIG. 2, the legs 195 and 198 are less spread apart than they are in FIG. 1.

FIG. 3 is a rear view of the rigid-flex treatment device illustrating the control panel 310 for operating the LED treatment device of the invention. Also illustrated in FIG. 3 is the back of the leg 195. The back of leg 195 is labeled 320. Also illustrated in FIG. 3 is the back of leg 198, which is labeled 340. In addition, FIGS. 3-7 illustrate the unique shape of the legs 320,340. The legs are wider at the top and narrower at the base. The reason for this structure is that when the curved arch 330 is placed over the face, the curved arch is supported by the legs, which rest on a spa table, massage bed, etc. In order for the curved arch to cover from the forehead to the neck, the device must be positioned as close to the shoulders as possible. With the legs narrower at the bottom, this allows the entire unit to be positioned closer to the shoulders of the patient; thus enabling the device to treat the entire face and a portion of the neck, as well.

Figure 4:
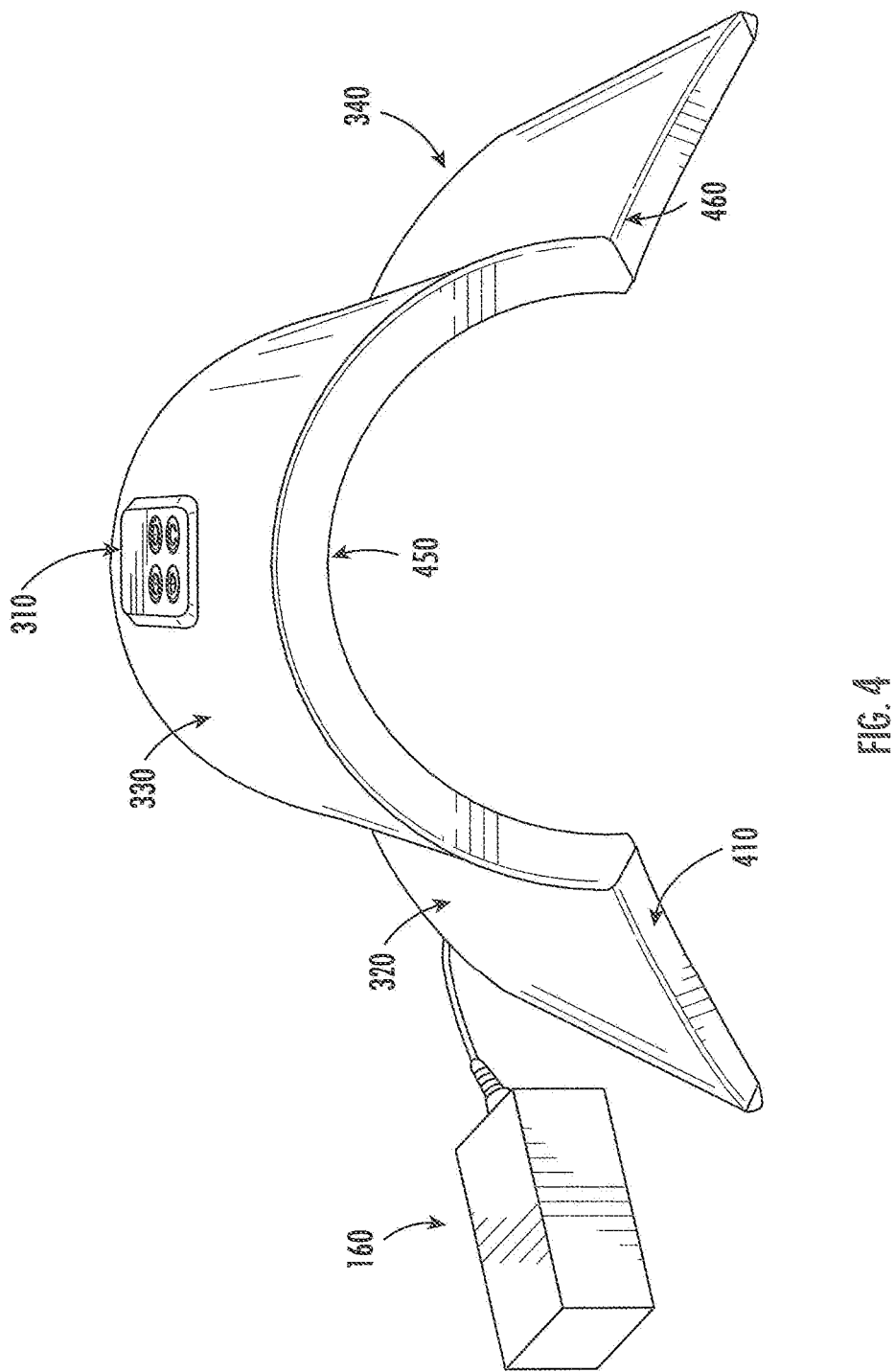
FIG. 4 is directed to a rear view of the invention with the legs moved outwardly to locate the LED bulbs closer to the face and head of the patient.

FIG. 4 is a bottom view of the hands-free LED treatment device for treatment of acne or treatment of wrinkles. FIG. 4 illustrates bottom surface 450 of the housing for the LED bulbs. Also illustrated in FIG. 4 is reference numeral 410 which represents the underside of the bottom of one of the legs and reference numeral 460 which represents the underside of the bottom of the opposite leg of the hands-free LED treatment device. The treatment for acne is different than the treatment of wrinkles. The treatment differs as a result of the different wavelengths used to treat acne and tire different wavelengths used to treat wrinkles. To treat wrinkles, the rigid areas with LED bulbs utilizes 126 LEDS of 605 nm, 210 LED bulbs of 630 nm, 126 LED bulbs of 660 nm and 126 LED bulbs of 850 nm. To treat acne, 280 LED bulbs of 415 nm and 210 LED bulbs of 630 nm are used. The different LED bulbs of the different wavelengths are distributed in the rigid areas having the LED bulbs. The distribution of the different wavelengths is as follows. As shown in FIG. 4, the legs 195 and 198 are hinged and they have a tension whereby they can be placed at any angle; and the wider the angle, the lower the arch 330 of the LED bulb housing lowers towards the face and head and neck of the patient being treated. This adjustment compensates for different sizes of peoples heads and also for different esthetic treatments that the clinician may be performing on the patient or client. For example, assume the clinician is performing a very invasive peel on the face and they want to use the LEDs immediately but do not want the treatment to be too intensive for the first LED treatment; in this situation, they would place the legs 195 and 198 straight, which pushes the arch the furthest from the face and reduces the intensity of the light. This results in the adjustable legs providing different unique benefits of: adjustment for different sizes and shapes of heads; and provide a lower or higher intensity of light.

Figure 5:
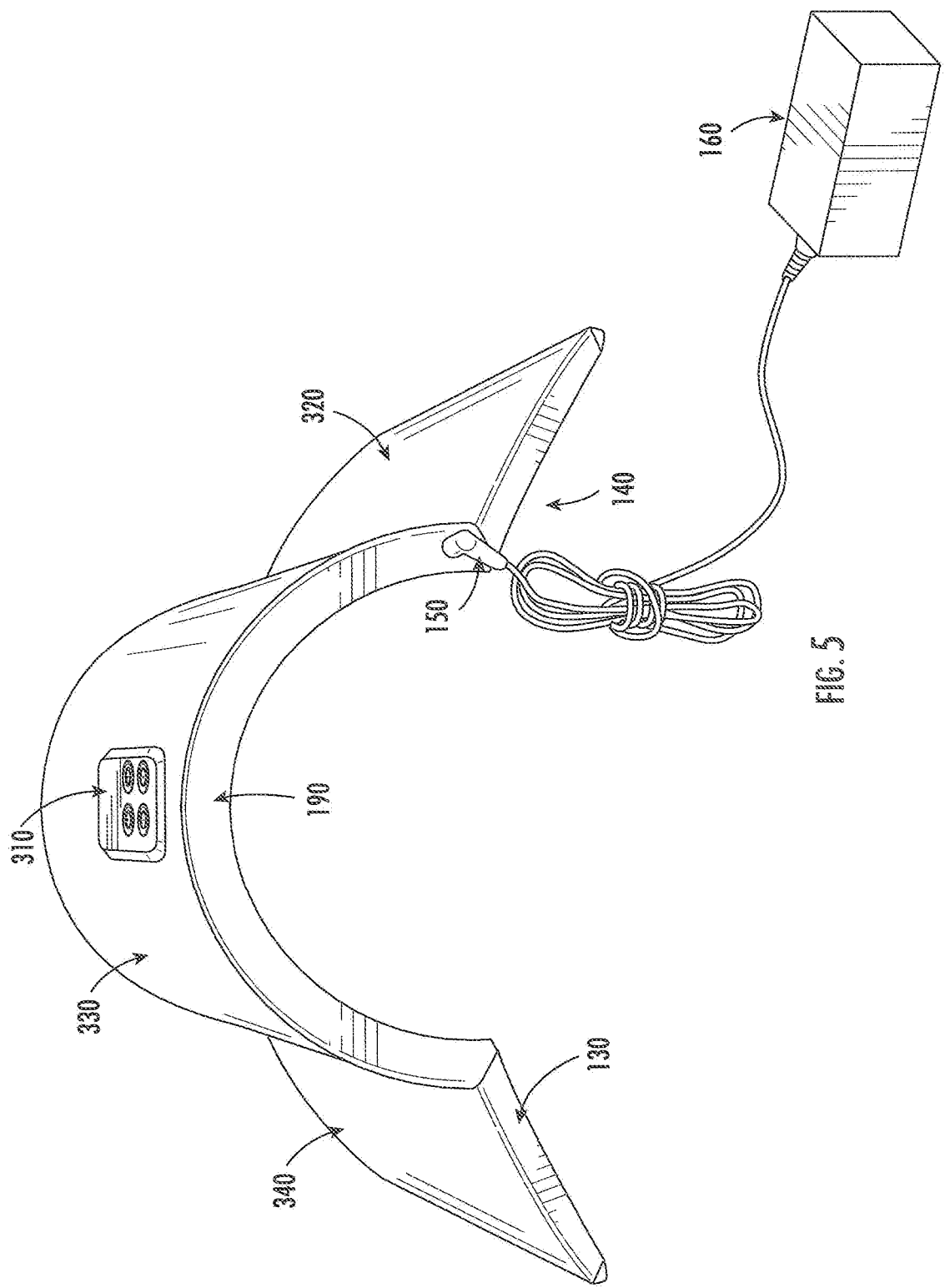
FIG. 5 Is directed to a perspective view of the invention illustrating the power supply, the control panel, and the outwardly extending legs.

FIG. 5 represents a perspective top view of the LED treatment device turned around from the view of FIG. 4. FIG. 5 illustrates the top surface 130 of one leg and the top surface 140 of the opposite leg. FIG. 5 additionally illustrates how the outward sideways location of the legs bring the LED bulb housing closer to the face and head of the patient being treated.

Figure 6:
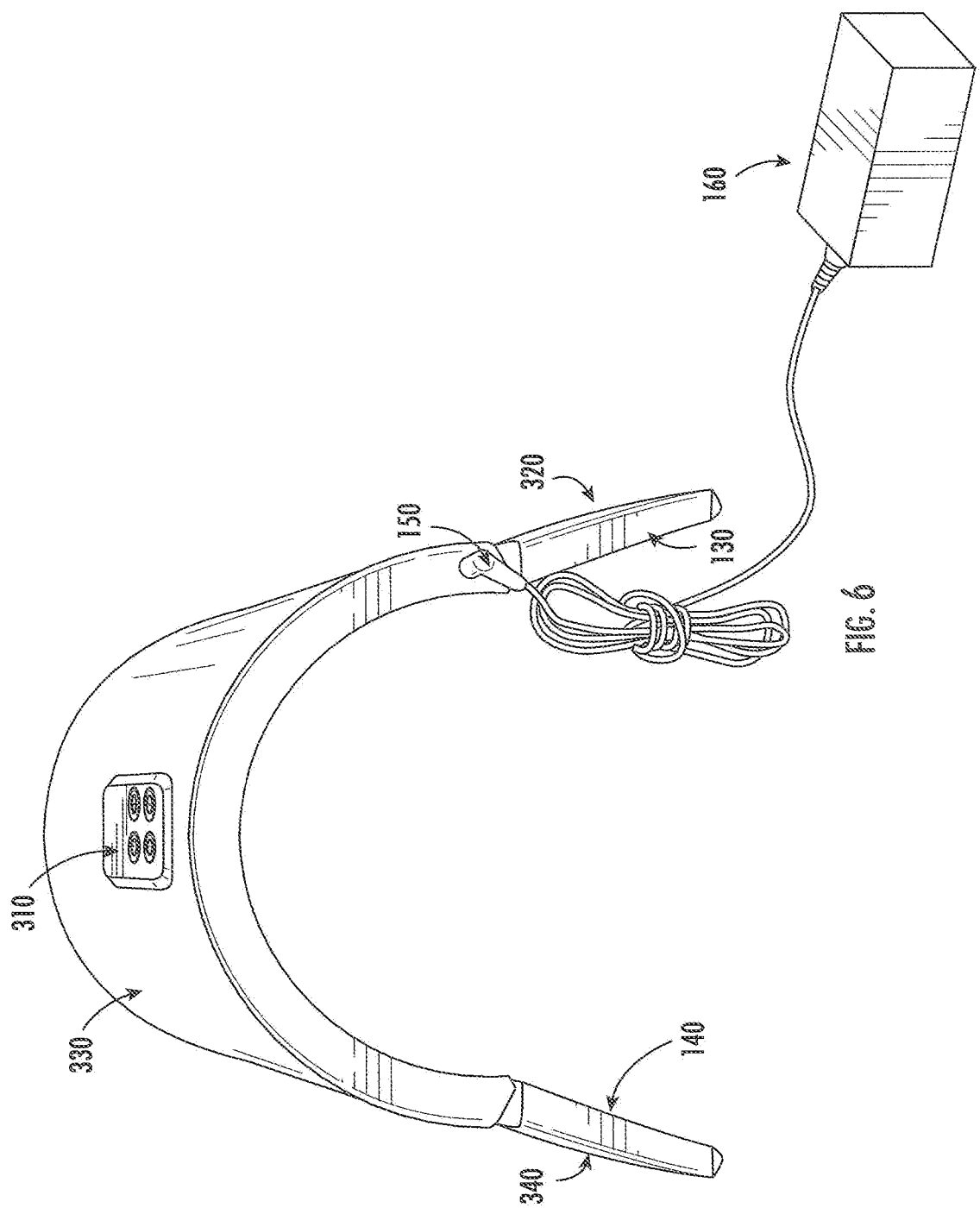
FIG. 6 is directed to a perspective view similar to FIG. 5, with the legs moved inwardly to raise the height of the LED bulbs from the face and head of the patient being treated.

FIG. 6 illustrates the legs being closer together to raise the LED bulbs further from the face and head of the patient being treated. FIG. 6 represents an exemplary embodiment that treats wrinkles or acne.

Figure 7:
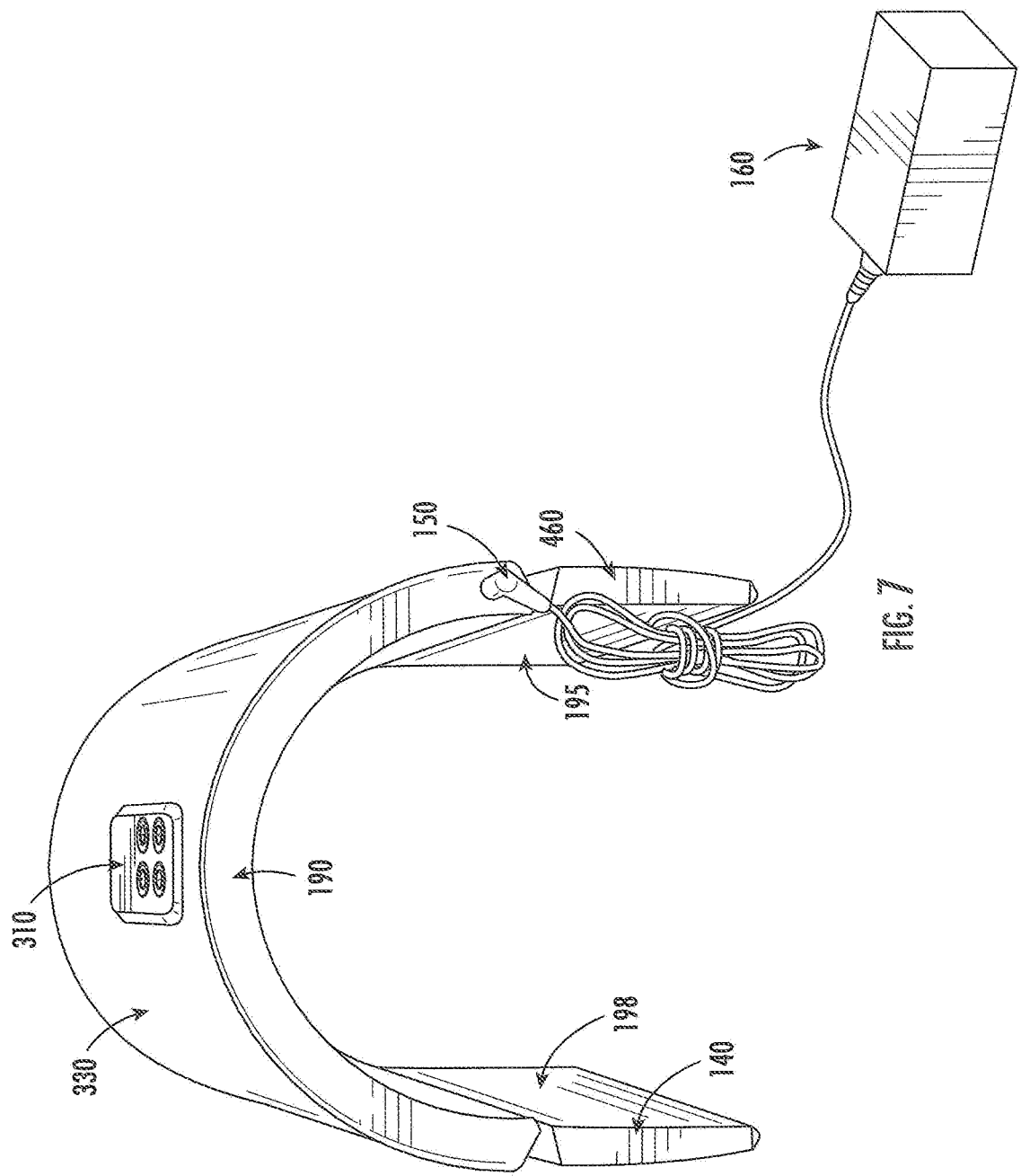
FIG. 7 is directed to a perspective view similar to FIG. 6, but with the legs moved fully vertical to raise the height of the LED bulbs from the face and head of the patient being treated.

FIG. 7 represents the moving the legs 195 and 198 to their highest position so that the LED bulbs are at their highest point from the face and head of the patient being treated. FIG. 7 represents an exemplary embodiment where hair loss is treated instead of wrinkles and acne. The locations of the legs in these figures are unrelated to the type of treatment being provided.

Figure 8:
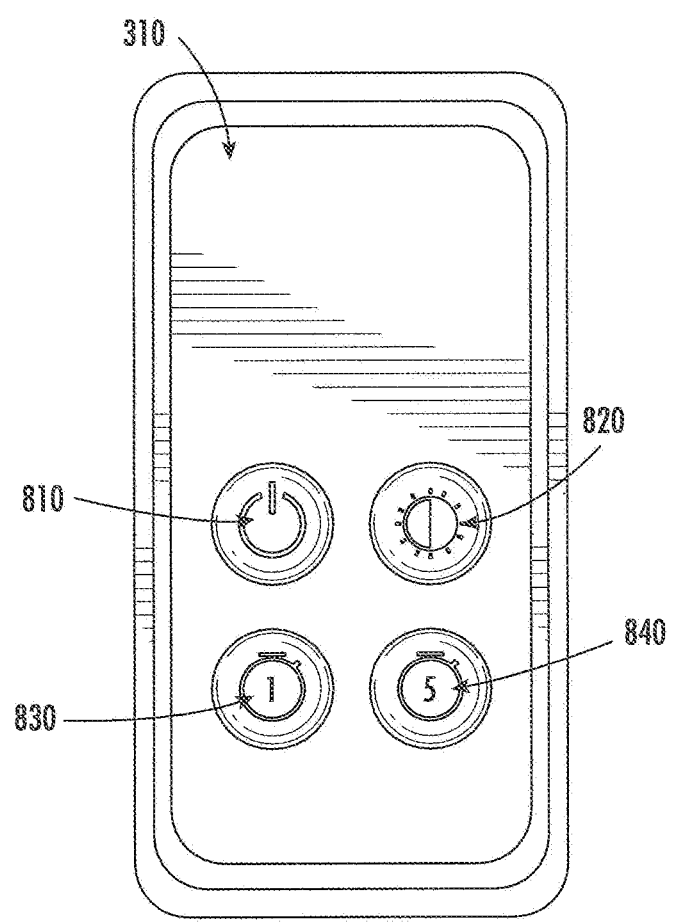
FIG. 8 is directed to an illustration of the control panel.

FIG. 8 illustrates the control panel 310, which controls the operation of the hands-free treatment device. Shown in the control panel of FIG. 8 are four buttons. The top left button is to turn the power to the hands-free treatment device on or off. The top right button represents a toggle to go switch between treatment of wrinkles or acne. Altenativiely, the top right button can represent treatment for hair loss. The bottom left button represents treatment for one minute. The bottom right button represents treatment for five minutes. Although four buttons are illustrated, more or less buttons may be provided, as would be readily understood by an artisan.

Figure 9:
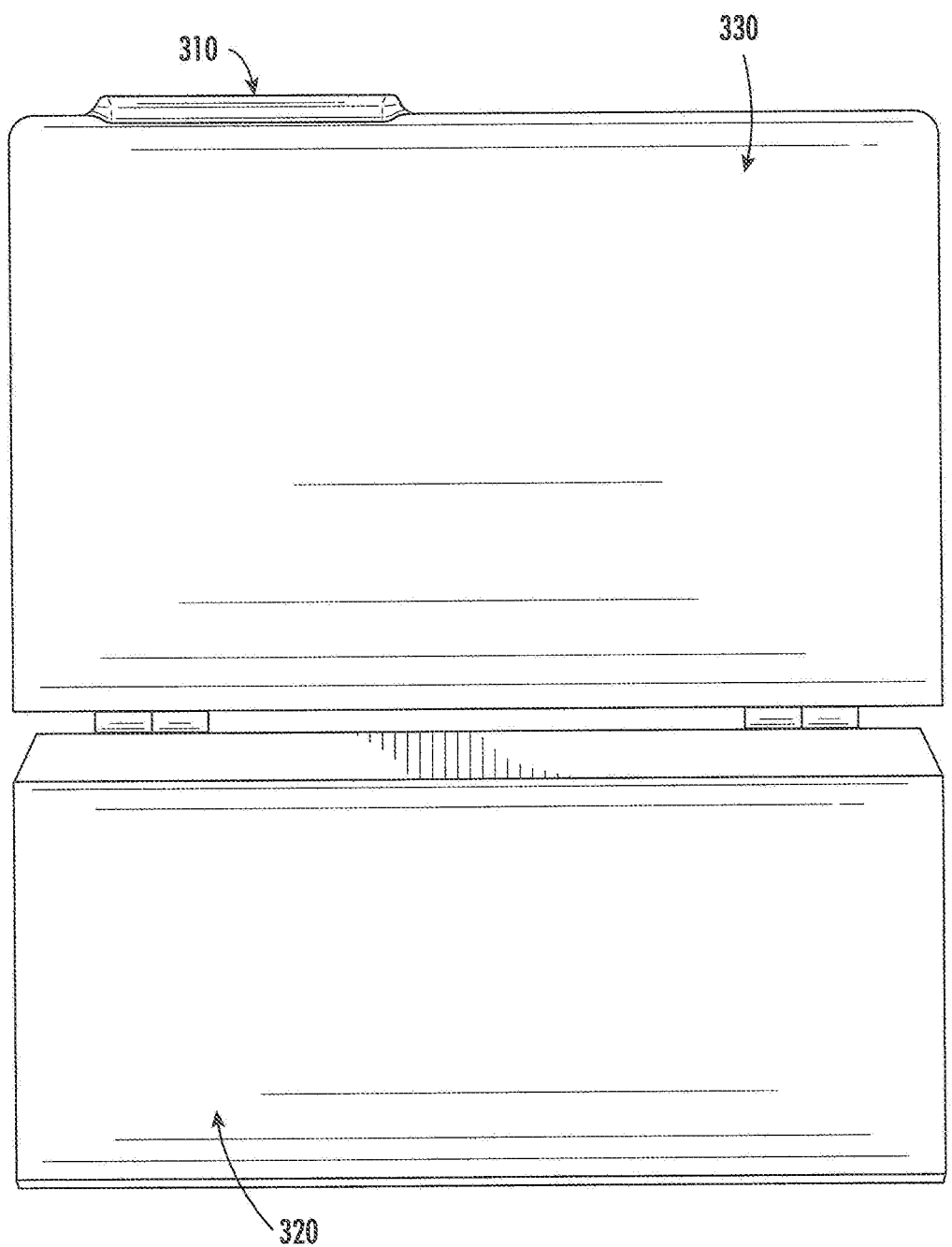
FIG. 9 is directed to a side view of the invention illustrating one of the legs; a side view of the control panel, with the adjustable hinges between the housing and the legs, and the housing with the LED bulbs.

FIG. 9 illustrates a side view of the rigid-flex LED treatment device for treating acme and Wrinkles or hair loss. FIG. 9 illustrates one of the legs 320, a side view 310 of the control panel, the adjustable hinges 170 between the LED bulb housing 330 and the leg 320.

Figure 10:
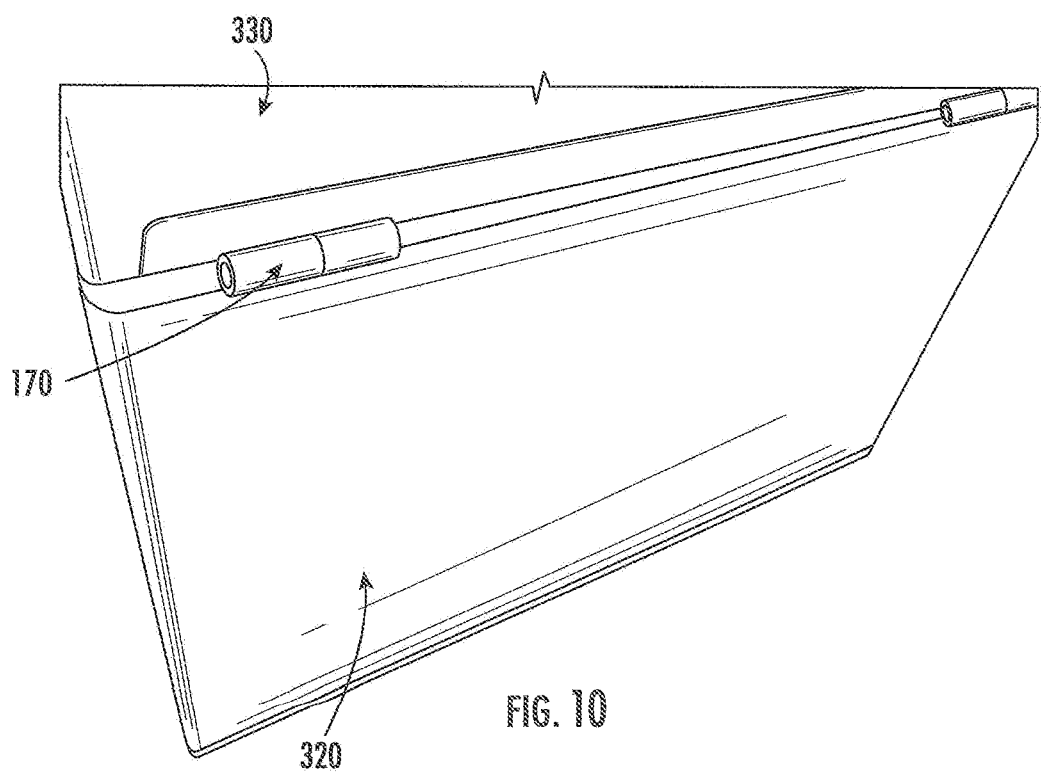
FIG. 10 is directed to a closeup view of a leg, the housing, and the adjustable hinges.

FIG. 10 illustrates one of the legs 320, the hinges on one side of the device and part of the arched or curved top 330 of the rigid-flex LED treatment device 100.

Figure 11:
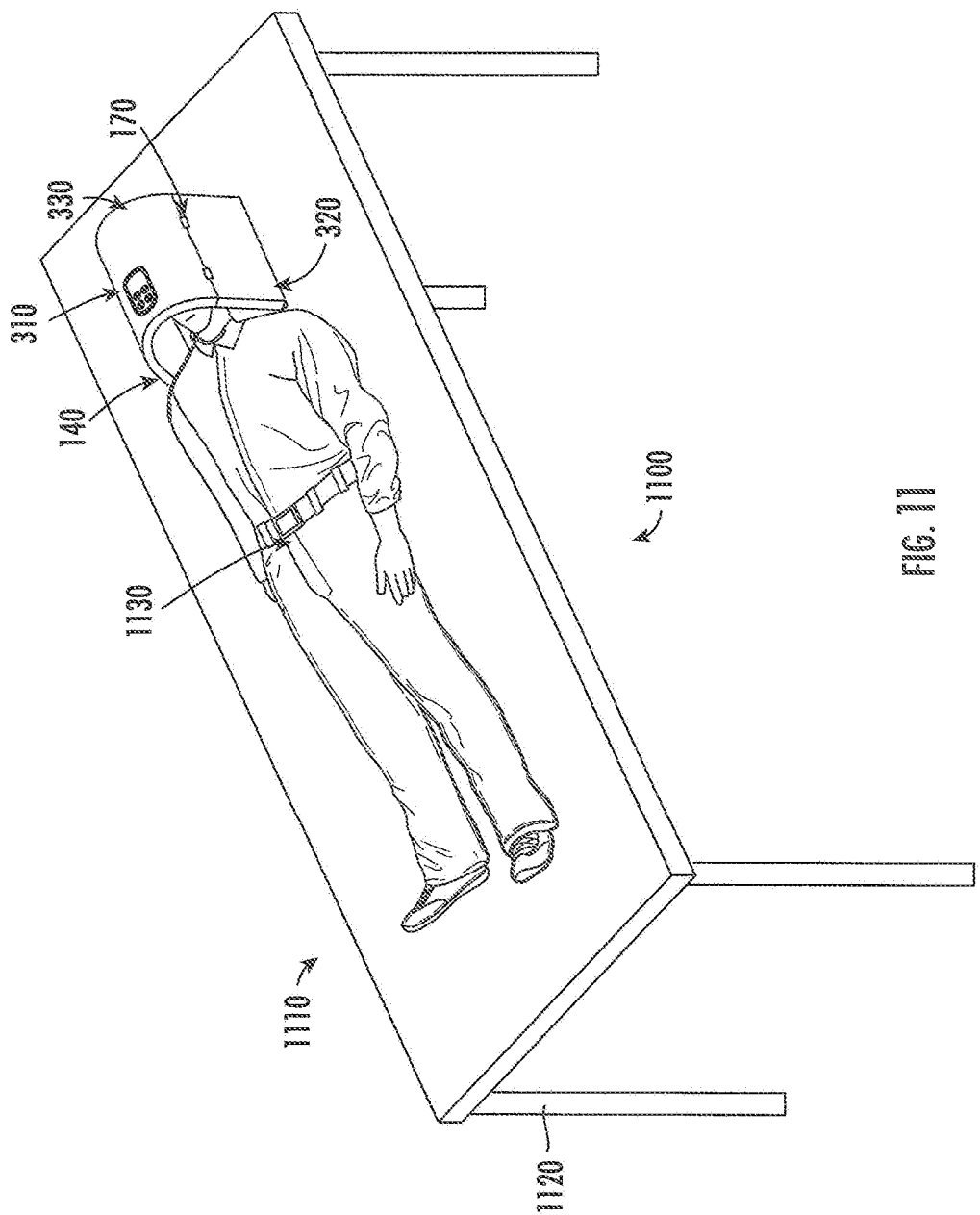
FIG. 11 is directed to a perspective view of a patient lying on a massage table with the LED treatment device in position to treat the patient's acne or wrinkles.

FIG. 11 illustrates a patient lying on a massage bed 1110, for treatment by a clinician. The massage bed includes legs 1120. Lying on top of the massage bed is a patient with the rigid-flex LED treatment device in position with the legs upright so that the rigid-flex LED bulb containing curved top 330 is over the face and neck of the patient. In addition, because the legs are in an upright position, the LED bulbs are at their furthest distance from the face and neck and head of the patient.

Although an exemplary embodiment of the invention with some variants has been shown and described, and an artisan would be aware of other embodiments. The claims are not to be limited to the disclosed invention but from the scope of the attached claims.

What is claimed is:

1. A hands-free LED device for the treatment of wrinkles and acne or hair loss for an entire face of a patient being treated, the device comprising:
   a housing containing both rigid and flexible areas;
   the rigid areas contain a large number of LED bulbs, which prevent the LEDs from breaking;
   the flexible areas allow the housing to be maintained in a fixed position without damage to the LED bulbs;
   there are several areas with the LEO bulbs having interspaced therebetween the flexible areas; such that between each of the rigid LED bulb areas is a flexible area that keeps the rigid areas separate from the flexible area;
   the housing being configured to have the LED bulb both above and surrounding the face and head of a patient being treated;
   a leg extending below the bottom of the housing, with a leg on each opposite side of the housing;
   the legs being wider at the top of each leg and narrower at the bottom of each leg;
   LED bulbs in the rigid areas of the housing; the legs are devoid of any LED bulbs;
   the LED bulbs being of one wavelength when hair loss is being treated; four different wavelengths when wrinkles are being treated and; and two different wavelengths when acne is being treated; depending on whether acne or wrinkles or hair loss are being treated.

2. The hands-free LED device for the treatment of wrinkles and acne or hair loss for an entire face of a patient being treated of claim 1, further comprising: the housing is in a curved configuration.

3. The hands-free LED device for the treatment of wrinkles and acne or hair loss for an entire face of a patient being treated of claim 1, further comprising: the size of the legs are configured to have the bottom of the legs abut the patient's shoulders.

4. The hands-free LED device for the treatment of wrinkles and acne or hair loss for an entire face of a patient being treated, of claim 3, further comprising; the size of the housing is configured to cover the entire face and part of the head of the patient being treated.

5. The hands-free LED device for the treatment, of wrinkles and acne or hair loss for an entire face of a patient being treated, of claim 1, further comprising: the legs are connected to the housing by hinges.

6. The hands-free LED device for the treatment of wrinkles and acne, or hair loss for an entire face of a patient being treated, of claim 5, further comprising: the hinges are adjustable to raise or lower the height of the housing closer or further from the face of the patient being treated, depending on the treatment being performed.

7. The hands-free LED device for the treatment of wrinkles and acne, or hair loss for an entire face of a patient being treated, of claim 1, further comprising: a control panel for operating the hands-free LED device for the treatment of wrinkles and acne, or hair loss for an entire face of a patient.

8. The hands-free LED device for the treatment of wrinkles and acne, or hair loss, for an entire face of a patient being treated, of claim 1, further comprising: for treatment of wrinkles, the LED bulbs are configured in four different wavelengths.

9. A hands-free LED device for the treatment of wrinkles and acne, or hair loss, for an entire face of a patient being treated, of claim 8, further comprising: for wavelengths for treatment of wrinkles are 605 nm, 630 nm, 660 nm, and 850 mn.

10. A hands-free LED device for the treatment of wrinkles and acne for an entire face of a patient being treated of claim 9, further comprising: the number of LED bulbs at each wavelength for treatment of wrinkles are: 126 LED bulbs of 605 nm; 210 LED bulbs of 630 nm, 126 LED bulbs of 660 nm, and 126 bulbs of 850 nm.

11. A hands-free LED device for the treatment of wrinkles and acne for an entire face of a patient being treated, of claim 8, further comprising: for treatment of acne, two different wavelengths are 414 nm and 630 nm.

12. The hands-free LEO device for the treatment of wrinkles and acne, or hair loss, for an entire face of a person being treated of, claim 11, further comprising: the number of LED bulbs at each wavelength are 280 LED bulbs at 415 nm and 210 LED bulbs of 630 nm.

13. The hands-free LED device for the treatment of wrinkles and acne, or hair loss, for an entire face of a person being treated, of claim 1, further comprising: the LED bulbs of specific numbers and different wavelengths are distributed throughout the rigid areas of the housing.

14. The hands-free LED device for the treatment of wrinkles and acne, or hair loss, for an entire face of a person being treated, of claim 1, further comprising: for treatment of hair loss only one wavelength of 630 nm is used and there are 500-700 ulbs for the hair-loss treatment.

15. The hands-free LED device for the treatment of wrinkles and acne, or hair loss, for an entire face of a person being treated, of claim 1, further comprising: the number of LED bulbs and the wavelengths together produce the treatments of the patient for wrinkles and acne, or hair loss.

16. A hands-free LED device for the treatment of wrinkles and acne, or hair loss for an entire face of a patient being treated, the device comprising:
a housing containing both rigid and flexible areas:
the rigid areas contain a large number of LED bulbs, which prevent the LEDs from breaking;
the flexible areas allow the housing to be maintained in a curved position;
the housing includes several areas with the LED bulbs having interspaced therebetween the flexible areas; such that between each of the rigid LED bulb areas is a flexible area that keeps each of the rigid LED bulb areas separate from the flexible areas;
the housing being configured to have the LED bulbs both above and surrounding the face and head of a patient being treated;
a leg extending below the bottom of the housing, with a leg on each opposite side of the housing;
the legs being wider at the top of each leg and narrower at the bottom of each leg;
LED bulbs are located in the rigid areas of the housing: the legs are devoid of any LED bulbs;
the wavelengths for treatment of wrinkles are 605 nm, 630 nm, 660 nm, and 850mn; and
the number of LED bulbs at each wavelength for treatment of wrinkles are: 126 LED bulbs of 605 nm; 210 LED bulbs of 630 nm, 126 LED bulbs of 660 nm, and 126 LED bulbs of 850 nm;
for treatment of acne, two different wavelengths are 414 nm and 630 nm; and
the number of LED bulbs at each wavelength for treatment of acne are 280 LED bulbs at
415 nm and 210 LED bulbs of 630 nm;
For treatment of hair loss, there are 500-700 LED bulbs and all are at 630 nm.

17. A hands-free LED device for the treatment of wrinkles and acne, or hair loss
for an entire face of a patient being treated, the device comprising:
a housing containing both rigid and flexible areas;
the rigid areas contain a large number of LED bulbs, which prevent the LEDs from breaking;
the flexible areas allow the housing to be maintained in a fixed position;
the there are several areas with the LED bulbs having interspaced therebetween the flexible areas; such that between each of the rigid LED bulb areas is a flexible area that keeps each of the rigid areas separate from the flexible areas;
the housing being configured to have the LED bulbs both above and surrounding the face and head of a patient being treated;
a leg extending below the bottom of the housing, with a leg on each opposite side of the housing;
the legs being wider at the top of each leg and narrower at the bottom of each leg;
LED bulbs in the rigid areas of the housing; the legs are devoid of any LED bulbs;
for treatment of acne, two different wavelengths are 414 nm and 630 nm; and
the number of LED bulbs at each wavelength for treatment of acne are 280 LED bulbs at 415 nm and 210 LED bulbs of 630 nm.

18. The hands-free LED device for the treatment of wrinkles and acne, or hair loss, for an entire face of a patient being treated of claim 17, further comprising: the size of the housing is configured to cover the entire face and the head of the patient being treated, the legs are connected to the housing by hinges and the hinges are adjustable to raise or lower the height of the housing closer or further from the face of the patient being treated, depending on the treatment being performed.

19. The hands-free LED device for the treatment of wrinkles and acne, or hair loss, for an entire face of a patient being treated of claim 17, further comprising: the housing is in a curved configuration and the size of the legs is configured to have the bottom of the legs abut the patient's shoulders.

20. The hands-free LED device for the treatment of wrinkles and acne, or hair loss, for an entire face of a patient being treated of claim 19, further comprising: the size of the housing is configured to cover the entire face and the head of the patient being treated, the legs are connected to the housing by hinges and the hinges are adjustable to raise or lower the height of the housing closer or further from the face of the patient being treated, depending on the treatment being performed.

* * * * *